United States Patent
Molnarne-Kahan

(10) Patent No.: US 6,949,241 B2
(45) Date of Patent: Sep. 27, 2005

(54) USE OF LACROPHYL PREPARATION IN EYE DROPS CONTAINING THERAPEUTICALLY ACTIVE COMPOUNDS

(76) Inventor: Ilona Molnarne-Kahan, Pozsonyl ut. 26, H-1137 Budapest (HU)

( * ) Notice: Subject to any disclaimer, the term of this patent is extended or adjusted under 35 U.S.C. 154(b) by 408 days.

(21) Appl. No.: 10/275,125

(22) PCT Filed: May 4, 2001

(86) PCT No.: PCT/HU01/00053
§ 371 (c)(1),
(2), (4) Date: Oct. 31, 2002

(87) PCT Pub. No.: WO01/82893
PCT Pub. Date: Nov. 8, 2001

(65) Prior Publication Data
US 2003/0124112 A1 Jul. 3, 2003

(30) Foreign Application Priority Data
May 4, 2000 (HU) .......................................... 0001769

(51) Int. Cl.[7] .............................................. A61K 31/74
(52) U.S. Cl. ................ 424/78.04; 424/94.6; 424/94.61; 514/252.13; 514/253.08; 514/397
(58) Field of Search .............................. 424/78.04, 94.6, 424/94.61; 514/252.13, 253.08, 397

(56) References Cited

U.S. PATENT DOCUMENTS 5,188,826 A * 2/1993 Chandrasekaran et al. ........................ 424/78.04
5,192,535 A * 3/1993 Davis et al. ............. 424/78.04

FOREIGN PATENT DOCUMENTS

WO 9117469 * 11/1991

* cited by examiner

Primary Examiner—Herbert J. Lilling
(74) Attorney, Agent, or Firm—Herbert Dubno

(57) ABSTRACT

The invention refers to the use of a lacrophyl preparation containing lysozyme, tris(hydroxymethyl)aminomethane, if desired other lacrophyl components, preferably ascorbic acid and/or citric acid and/or ethylenediamine-tetraacetic acid, in the rest distilled water for the dissolution of an active substance being insoluble or only slightly soluble in water or physiological saline, for preparing eye-drops, and/or in case of eye-drops containing an active substance to adjust optionally an active substance medium appropriate to the composition of the native tear and for the microbiological protection of the medium.

13 Claims, No Drawings

USE OF LACROPHYL PREPARATION IN EYE DROPS CONTAINING THERAPEUTICALLY ACTIVE COMPOUNDS

The invention refers to the use of a lacrophyl preparation providing microbiologic protection for eye-drops containing therapeutically active compounds.

It is well known that preservatives generally used in eye-drops are not indifferent. In some cases the preservative reacts with the therapeutically active compound and so the solution of the therapeutically active compound form is an insoluble complex with the preservative and gets slowly separated from the solution (Dreiler van der Glas, Bult A.: Incompability of indometacin and benzalkonium in eye-drops due to ion-pair formation. Pharmaceutiche Weekblad 9, 29–32, 1987). In several patients preservatives provoke allergical symptoms (e.g. mercury allergy against thiomersal).

In very small concentrations (0.0001% benzalkonium-chloride) causes cell death. In small concentrations it causes apoptosis, in greater concentration necrosis may occur. (De Saint Jean M. et al. proved it in vitro (Invest. Ophthalmol. Vis. Sci. 40, 619–630, 1999).

As it is well known, preservatives in eye-drops almost without exception exert detrimental side-effects, also when no allergy occurs. Short term application does not cause visible deterioration of the cornea, but in case of permanent application, when the patient is obliged to apply eye-drops throughout his whole life e.g. in the case of glaucome or "dry-eye" the impairment of the cornea gets visible.

The side-effect above can be eliminated if no preservatives are used by the manufacturer. Since without this the eye-drops get easily be infected, once to be used eye-drop packaging are used. This is practically an eye-drop solution sealed up in a short pipette. The patient drops from this solution in his eye and throws it away after once used This method is expensive and for the patient it means a considerable burden. At the manufacturer the expenses are significantly greater than at the traditional packaging. Still greater expenses reveal at the patient. In addition, the patient gets in an inconvenient situation, since if he leaves his permanent home, he has to take a considerable amount of packages with him.

Numerous eye-drops contain therapeutically active compound which are insoluble or only slightly soluble in water or physiological saline. In these cases solvents or intermediate agents are used, usually these are of no lacrophyl nature. Although these can be used for the solution of the therapeutically active compound, but they are present as foreign substances and they disturb in many cases the physiological environment of the eye disadvantageously.

For the preparation of eye-drop solutions "solutio ophthalmica" and "solvents pro oculogutis" are used, etc. These contain also benzalkonium chloride or phenylmercuriborate for the protection against bacterial infection. In the past last years it has been proved that tear production diminishes under the action of some substances and also the composition might change. E.g. it is known that in the lower layer of the tear present mucin is coating the foreign substances of artificial tears like PVA (polivinylalcohol), PVP (polivinylpirrolidone) or MCE (methylcellulose) and thus they are removed through the lacrimal canal. And through this fact the amount of the important role playing mucin is diminishing, their amount will be steadily smaller.

Those persons using soft contact lenses cannot utilize at all the artificial tear preparations referred to above due to the danger of sedimentation and the clogging of the pores of the soft contact lens.

According to the state of the art such a lacrophyl preparation is not known which would be suitable to solve the complex problems outlined above.

It is known that lacrimal production decreases considerably in patients suffering from the Sjögren syndrome. Tear production decreases similarly in the elderly in a smaller rate.

Some virus infections e.g. the herpes virus and the adenovirus infection can cause the decrease of tear lysozyme content. (Gupta et al.: Immuno assay of tear lysozyme in acute adenovirus conjunctivities. Brit. J. Ophtlalmol. 70, 439, 1986).

Medicines can also cause the decrease of the amount of tear lysozyme. This was observed in the case of glaucome, when timolol or cartelol was dropped in the eye (Practolol syndrome) (Yumita A. et al.: The long-term effect of topical therapy with cartelol, an adrenergic beta blocking agent on tear lysozyme. Acta XXV Concilium Proc. Int. Congress Ophthalmol. Rome 1986. Ophthalmologicum Kugler, Cinedim Amsterdam, 1987).

From the Hungarian patent No. 200 276 a procedure for preparing a tear substitute containing lysozyme and some other lacrophyl substances became known, which contain as principal component egg white lysozyme, enzyme activating substances and beside these other lacrophil, natural substances, the antiphlogistic ascorbic acid and/or citric acid. According to the patent cited the most important effect of lysozyme is that not merely the eye is protected by it against infections, but the solution itself is also protected against infections.

WO 91 17469 relates to a kit for contact lenses containing lysozyme, ascorbic and citric acid as active compounds to provide an appropriate tear substitute in form of a lacrophyl solution. The dissolution of poorly water soluble active agents is not contemplated by this documents.

WO 92 0044 (Insite Vision) suggests to use polymers to the dissolution of pharmaceutically active agents such as pilocarpine or fluorometholone. The suggested polymers need a stabilizer, further the polymer may be used only in acidic medium which causes all irritation of the eye.

Object of the invention is the preparation of eye-drops containing the regular therapeutically active compounds without using preservatives, also with some of those therapeutically active substances which are insoluble or only slightly soluble in water or physiological saline. It was our intention also to avoid deterioration of the aqueous solution of eye drops for at least one week-one month, and they should be protected against bacterial contaminations, The maintenance of the composition of the natural tearfluid is also an important problem to be solved in some diseases and in the elderly.

The invention relates to the use of lysozme, tris (hydroxymethyl)aminomethane, if desired natural lacrophyl substances, preferably ascorbic acid, and/or citric acid, boric acid and/or ethylenediamine-tetraacetic acid and in the rest distilled water containing preparation for the dissolution of a therapeutically active substance insoluble or only slightly soluble in water to produce eye-drops drops and/or for adjusting the optimal composition of an eye-drop containing active substance in respect to the chemical reaction (pH), and osmotic pressure nearly equal to that of the natural tearfluid. (Ethylenediamine-tetraacetic acid keeps $Ca^{++}$ in solution, inhibits action of collagenase and hereby protects the collagene structure of the cornea (Kahánné, L. I.: The biochemistry of the eyesight, Medicina, 1986). The lacrophyl preparation is employed in a tenfold or rather in a hundredfold excess calculated on the amount of the active substance of the eye-drop.

Eye-drops prepared by using the ingredients referred to do not cause corneal damage even if they are permanently used. Though lysozyme applied systematically can cause allergic reactions (Verhamme et al.: Internat. Pharmac. J. 2, 129–132, 1988). Using lacrophyl eye-drop solutions, locally applied there is no such experience (Pálfalvi M., Kahán I. L.: Efficacy and retention time of a new tear substitute, Acta Ophthalm. 71, 836–838, 1993). At the same time stability of the eye-drops remains about 1–2 years without employing preservatives, and after the dissolution of the active substance it can be used for one week to one month.

The active substance might be an antibiotic, e.g. rifampicin or doxycycline, minocycline, oxy-tetracycline or some other tetracycline derivative, ciprofloxacine hydrochloride, in the treatment of glaucoma used pilocarpine, levobunolone and timolol-maleate, a steroid like fluorometholone and for diagnostic purpose used fluorescein-sodium. A precondition of the eye-drop stability: the preparation for dissolving the active substance should contain nearly the same lysozyme concentration as that of tears, moreover the reaction (pH) of the eye-drop, and the osmotic pressure should be nearly equal to that of the tear.

In the eye-drops we used egg-white lysozyme (EC 3.2.1.17) isoenzyme of tear lysozyme to which the above-mentioned substances were added for adjusting the appropriate reaction (pH) and osmotic pressure. By means of that no separate intermediate and use of an eye-drop preservative is necessary.

It could be established that adding artificially germs into the tested eye-drop solution they perished in 100 percent, in the case of bacteria (*Echerishia coli, Pseudomonas aeruginosa, Staphylococcus aureus*) during 5 weeks, in the case of fungi (*Candida albicans, Aspergillus niger*) during 4 weeks, respectively.

EXAMPLE 1

| Rifampicin eye-drop | |
| --- | --- |
| Rifampicin | 0.02 g |
| Lacrophyl eye-drop solvent preparation: | |
| EDTA-Na₂ | 0.01 g |
| Lysozyme HCl | 0.01 g |
| tris(hydroxymethyl)aminomethane | 0.27 g |
| boric acid | 0.05 g |
| citric acid | 0.164 g |
| distilled water | ad 10 ml |

The in advance prepared "lacrophyl" preparation was supplied to the weighed rifampicin and was intensively shaken. The so prepared eye-drop can be used in cases of the eye's virus infection, e.g. adeno-virus or herpetic infection and in the case of swimmer's conjunctivitis. In case of packaging is effected into a two parts eye-drop bottle in which the active substance and the solution is separated in two parts, the storage is possible for two years. If rifampicin and the "lacrophyl" solvent is stored in 2 parts and gets into use only after rupture of the separation wall after shaking, then the shaked and to be used preparation can be applied for one month.

EXAMPLE 2

| Doxycycline eye-drop | |
| --- | --- |
| Doxycycline hydrochloride | 0.05 g |
| lacrophyl eye-drop preparation | 10.00 g |

EXAMPLE 3

| Pilocarpine eye-drop 1% | |
| --- | --- |
| Pilocarpine chloride | 0.1 g |
| lacrophyl eye-drop preparation | 10.00 g |

EXAMPLE 4

| Fluorescein sodium eye-drop | |
| --- | --- |
| Fluorescein sodium | 0.10 g |
| lacrophyl eye-drop preparation | 10.00 ml |
| the reaction of the solvent pH = 7.3 | |

What is claimed is:
1. A method of preparing a biologically protected eye drop composition comprising a pharmaceutically active substance that is insoluble or only slightly soluble in water or physiological saline, which comprises the step of:
   applying under intense shaking to the pharmaceutically active substance, a lacrophyl preparation which comprises:
   (a) 0.1 to 1.0 weight % of egg white lysosoze;
   (b) 0.18 to 3.6 weight % of tris(hydroxymethyl) aminomethane; and
   (c) a natural lacrophyl comprising:
      (I) 0.5 to 1.0 weight % of citric acid;
      (ii) 0.5 to 1.0 weight % of boric acid; and/or
      (iii) 0.5 to 1.0 weight % of EDTA; and
      (iv) 0 to 10.0 weight % of ascorbic acid; and balance distilled water, in an amount effective to dissolve the pharmaceutically active substance in the lacrophyl preparation and to microbiologically protect the resulting eye drop composition.
2. The method of preparing a biologically protected eye drop composition defined in claim 1 wherein the pharmaceutically active substance that is insoluble or only slightly soluble in water or physiological saline is selected from the group consisting of an antibiotic, a compound for treating glaucoma, a steroid and a diagnostic agent.

3. The method of preparing a biologically protected eye drop composition defined in claim 2 wherein the antibiotic is selected from the group consisting of rifampicin, a tetracycline, or ciprofloxacine hydrochloride.

4. The method of preparing a biologically protected eye drop composition defined in claim 2 wherein the compound for treating glaucoma is pilocarpine, levobunolone, or timolol maleate.

5. The method of preparing a biologically protected eye drop composition defined in claim 2 wherein the steroid is a fluorometholone.

6. The method of preparing a biologically protected eye drop composition defined in claim 2 wherein the diagnostic agent is fluorescein-sodium.

7. A biologically protected eye drop composition which comprises a pharmaceutically active substance that is insoluble or only slightly soluble in water or physiological saline, dissolved in a lacrophyl preparation which comprises:
   (a) 0.1 to 1.0 weight % of egg white lysosome;
   (b) 0.18 to 3.6 weight % of tris(hydroxymethyl) aminomethane; and
   (c) a natural lacrophyl comprising:
      (I) 0.5 to 1.0 weight % of citric acid;
      (ii) 0.5 to 1.0 weight % of boric acid, and/or
      (iii) 0.5 to 1.0 weight % of EDTA ; and
      (iv) 0 to 10.0 weight % of ascorbic acid; balance distilled water, in an amount effective to dissolve the pharmaceutically active substance and to microbiologically protect the resulting eye drop composition.

8. The biologically protected eye drop composition defined in claim 7 wherein the pharmaceutically active substance that is insoluble or only slightly soluble in water or physiological saline is selected from the group consisting of an antibiotic, a compound for treating glaucoma, a steroid and a diagnostic agent.

9. The biologically protected eye drop composition defined in claim 8 wherein the antibiotic is selected from the group consisting of rifampicin, a tetracycline, or ciprofloxacine hydrochloride.

10. The biologically protected eye drop composition defined in claim 8 wherein the compound for treating glaucoma is pilocarpine, levobunolone, or timolol maleate.

11. The biologically protected eye drop composition defined in claim 8 wherein the steroid is fluorometholone.

12. The biologically protected eye drop composition defined in claim 8 wherein the diagnostic agent is fluorescein-sodium.

13. A method of applying a pharmaceutically active ingredient that is water insoluble or only slightly water soluble to an eye of a patient, which comprises the step of topically administering to the eye of the patient, a pharmaceutically effective amount of the pharmaceutical composition defined in claim 7.

\* \* \* \* \*